United States Patent [19]

Hyman et al.

[11] Patent Number: 4,576,154

[45] Date of Patent: Mar. 18, 1986

[54] SACROILIAC BELT

[76] Inventors: Alan A. Hyman, 2800 N. Sheridan Rd., #610; Julie E. Goldberg, 3930 N. Pine Grove, both of Chicago, Ill. 60657

[21] Appl. No.: 595,590

[22] Filed: Apr. 2, 1984

[51] Int. Cl.4 ............................................. A61F 5/02
[52] U.S. Cl. ...................................... 128/78; 128/100
[58] Field of Search ...................... 128/95, 96, 99, 100, 128/68, 69, 78, DIG. 15, 87 R

[56] References Cited

U.S. PATENT DOCUMENTS

| 3,399,669 | 9/1968 | Kaplan | 128/78 |
|---|---|---|---|
| 3,442,270 | 5/1969 | Steinman | 128/DIG. 15 X |
| 3,535,719 | 10/1970 | Murcott | 128/DIG. 15 X |
| 3,587,570 | 6/1971 | Kilbey | 128/DIG. 15 X |
| 3,970,079 | 7/1976 | Gaylord, Jr. | 128/78 |
| 4,348,774 | 9/1982 | Woodson | 128/95 X |

OTHER PUBLICATIONS

IEM Orthopaedic Systems, Inc., The Lumbo Pelvic Support, 2 pages.

*Primary Examiner*—Richard J. Apley
*Assistant Examiner*—Alan W. Cannon
*Attorney, Agent, or Firm*—Cook, Wetzel & Egan, Ltd.

[57] ABSTRACT

An orthopedic belt eases sacroiliac joint pain by compressing soft pelvic tissue against the sacrum and ilium, to support and immobilize the sacro-iliac joints. The belt consists solely of flat, woven webbing forming a band about four to six inches wide, and a fastening device at the front. The belt encircles the patient at the level between the anterior superior iliac spines and the greater trochanters of the femurs. It is fastened with enough tension to compress the soft tissue as desired. Ends of the band forming the belt are fastened together at an angle which is selected to pass the belt horizontally across the back and to accommodate the shape of the patient's hips. The ends of the band are cut off in a taper if necessary so that no square corners are exposed. Various fastening means to place and maintain tension on the band may be used, including flexible straps extending from one end of the band through loops on the other and back to the first end, where they are connected together with cooperating press-holding pads such as Velcro TM hook and eye material.

1 Claim, 5 Drawing Figures

SACROILIAC BELT

The present invention relates to orthopedic devices for supporting and restraining joints in the human body, particularly in the sacro-iliac region, for purposes of easing pain and discomfort and to promote healing of ligaments.

Prior art corsets are generally worn too high to be effective for relieving pain in the sacroiliac joint. Known sacroiliac belts or supports use sacroiliac pads or stays rather than flat webbing.

Objects of the present invention include the provision of a sacroiliac belt which is simple and straightforward in its construction and use, very inexpensive to make, washable to preserve personal hygiene, and safe and effective for the relief of pain and discomfort in the sacroiliac joint. Further objects include the provision of a sacroiliac belt which can be constructed either on a custom basis or in a fixed variety of sizes and angular configurations to fit the great majority of patients.

The present invention in summary comprises a sacroiliac belt for orthopedic use consisting of a band of flexible webbing or like material which is substantially inextensible in length and flat over its width and length. The belt is used with no stays or pads over the sacrum. It is adapted to be fastened about the pelvis of a human patient beneath the iliac crests and over the coccyx. The band lies horizontally across the back of the user and is tensioned and fastened at the front. The band compresses the soft tissue of the pelvis against the sacrum and ilium, to support and restrain relative movements of the bones and thus to ease pain in the sacroiliac joint. The band is adapted to the curvature of the hips of the user by being joined at the front at an angle dependent on the hip contours. Various fastening means can be used, but a preferred form is the use of flexible straps connected to one end of the band, passed through loops connected to the other end of the band, and then fastened back to themselves using opposing pairs of press-holding pads such as Velcro ™ hook and eye material. The straps are conveniently aligned with the length of the band, but the loops are angled to cooperate with the direct pull of the straps, to enable firm tensioning of the band as desired.

Figure 1:
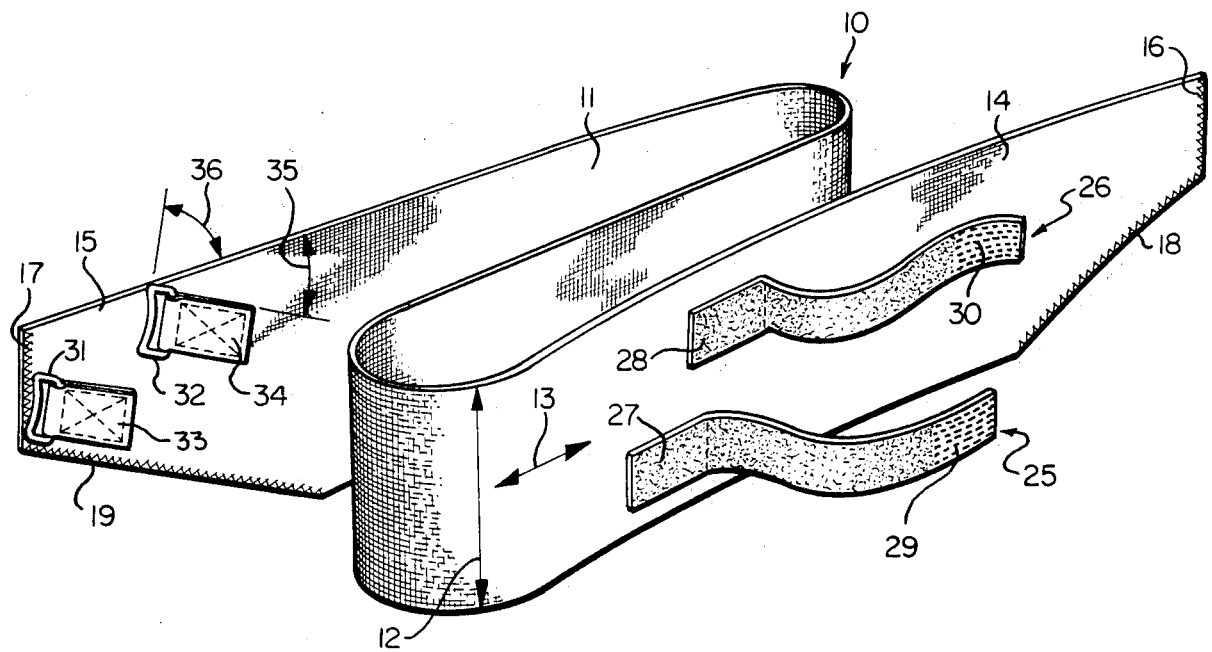
FIG. 1 shows, in a general perspective view, a sacroiliac belt embodying the principles of the invention.

As shown in the drawing figures, a sacroiliac belt 10 comprises a band 11 of an appreciable width 12 transverse to its length 13 between opposing ends 14, 15. The band 11 is flexible as shown but is substantially inextensible over its length 13. In one form the band 11 is made of two widths of two-inch wide woven cotton webbing material, such as is commonly used for shoulder bracing and the like, to provide a four-inch wide strip. The cotton (or cotton polyester or similar) material is washable and, because it is woven, breathes freely even when worn immediately adjacent to the skin of the user. Severed end portions 16, 17 and tapered bottom portions 18, 19 are sewn with overedge stitches to prevent unraveling. In synthetic fiber materials are used, the cutting can be done with heat means to prevent unraveling.

In accordance with the principles of the invention, no sacroiliac pad or rigid or flexible stays are provided at the center of the band 11. Such pads and stays have been universally used in the prior art, apparently because of a belief that they help to immobilize the sacral joints. Dispensing with such pads and stays lessens the cost of the belt. It importantly also reduces undesired upward shifting of the belt on the user's hips. Both advantages are achieved without reduction in medical effectiveness, because of the realization that it is principally the sidewards compression of the tissues about the sacroiliac joints which immobilizes them and reduces pain, not any radially inward compression applied by the pad or stays.

The length 13 of the band 11 is sufficient between the ends 14, 15 to encircle a user below the iliac crests and about the sacrum. The ends 14 and 15 of the band 11 are joined together in one embodiment by flexible straps 25, 26, each having one end 27, 28 firmly affixed to the band 11. The lengths of the straps 25, 26 are aligned with the length 13 of the band 11. The main portion of each strap 25, 26 is conveniently formed of one of two parts of cooperating press-holding material such as Velcro ™ hook and eye material, while the free ends 29, 30 comprise the other part thereof. The opposite end 15 of the band 11 carries loops 31, 32 on tabs 33, 34 stitched thereto.

Each tab 33, 34 is arranged at an angle 35 to the length 13 of the band 11, thereby presenting the loops 36 at a complimentary angle 36 to the length of the band 11. The angle 35 is selected to adapt the band 11 to the hip profile of a user, as discussed below. The loops 31, 32 receive the straps 25, 26, and turn them 180° so that the press-holding pads 29, 30 on the free ends of the straps 25, 26 can be pressed against the body of the straps after the band 11 is tightened about the user. This maintains a desired degree of compression of the soft tissues of the pelvis. The lower edges of the band 11 at the ends 14, 15 are tapered at the angle 35, as at 18, 19, to avoid having substantial amounts of free corner material exposed when the belt 10 is in use.

Figure 2:
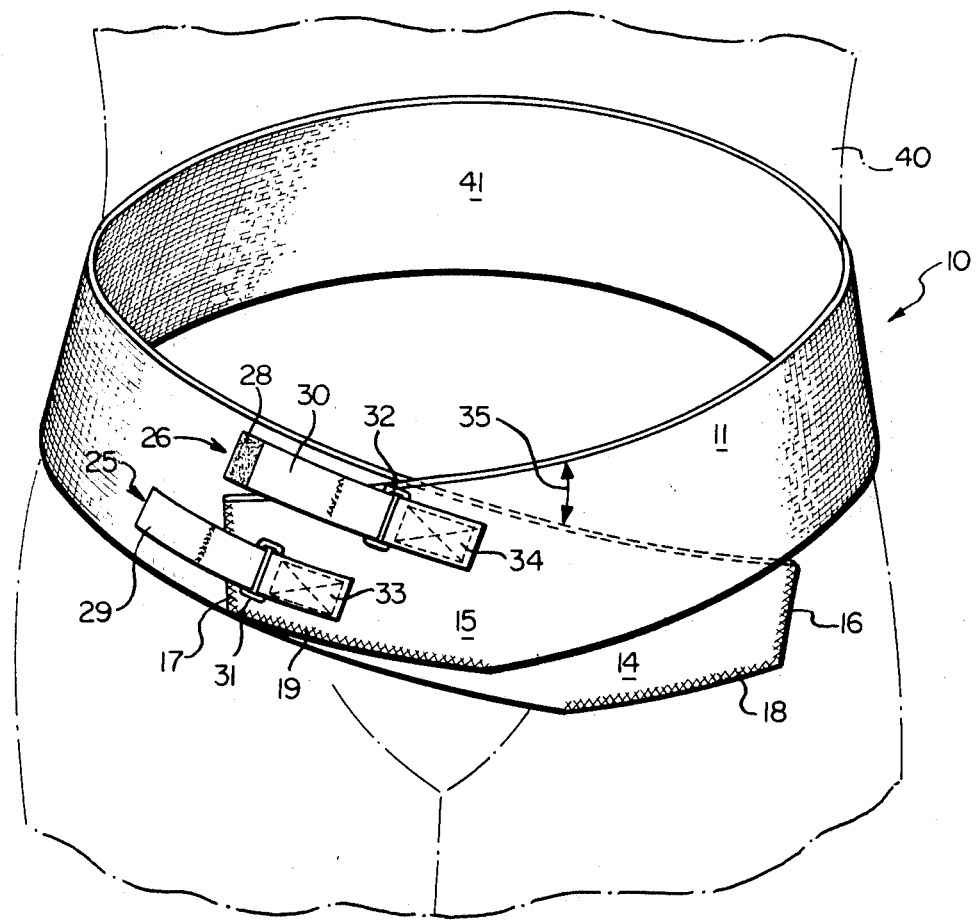
FIG. 2 is a general perspective view showing the configuration of the sacroiliac belt of FIG. 1 in use on a human patient (shown in phantom)
Figure 3:
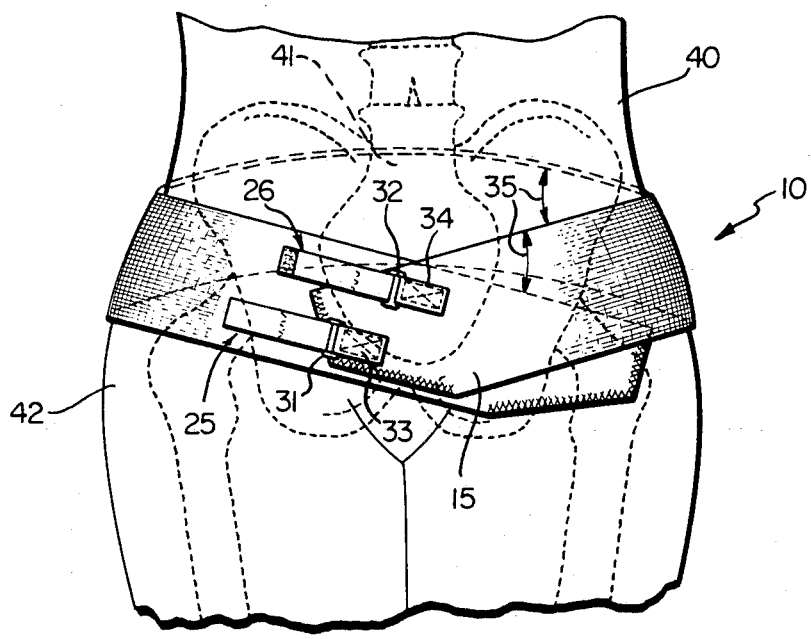
FIG. 3 is a front elevation view of the belt and user of FIG. 2, showing in phantom the internal bone structure of the pelvic region.

FIGS. 2 and 3 show the belt 10 as it is worn by a patient 40. The band 11 passes generally horizontally at its center portion 41 across the back of the user 40, directly outward of the sacrum, as shown. If the shape of the pelvis 42 of the patient 40 necessitates, the ends 14, 15 of the band 11 are tilted downward in the front as shown in FIGS. 2 and 3. In the elevational view, the angle 35 between the horizontal and the downward tilt of the ends 14, 15 is substantially the same as the angle 35 at which the tabs 33, 34 are affixed to the end 15 of the band 11.

The belt 10 is applied to the patient 40 by being encircled around his pelvis above the hips 42, with the flat, center portion 41 of the band 11 in a horizontal position. The straps 25 and 26 are passed through the loops 31 and 32, respectively, after the ends 14 and 15 of the band 11 are crossed at the front of the patient. The straps 25, 26 are then tightened, pulling the ends 14, 15 of the band 11 past one another to shorten the effective length of the band. The angling of the tabs 33, 34 and the loops 31, 32 evenly compresses the soft tissue of the pelvis 42 and of the back of the user 40 across the middle 41 of the band 11. Once the band 11 in cinched as tightly as is desired, the free ends 29, 30 of the straps 25, 26 are pressed against the bodies of the straps 25, 26, to retain the band 11 at its desired, effective length.

Tension as applied by this belt 10 appears to squeeze or compress the soft tissue of the pelvis, effectively supporting and immobilizing the bones with respect to each other. Pain or discomfort arising from stress or injury to the sacroiliac joints is eased. The belt has proven to be entirely or noticeably helpful in easing sacroiliac pain in over two thirds of the patients for whom the belt has been prescribed; in the remaining patients, no adverse effects were noted.

Figure 4:
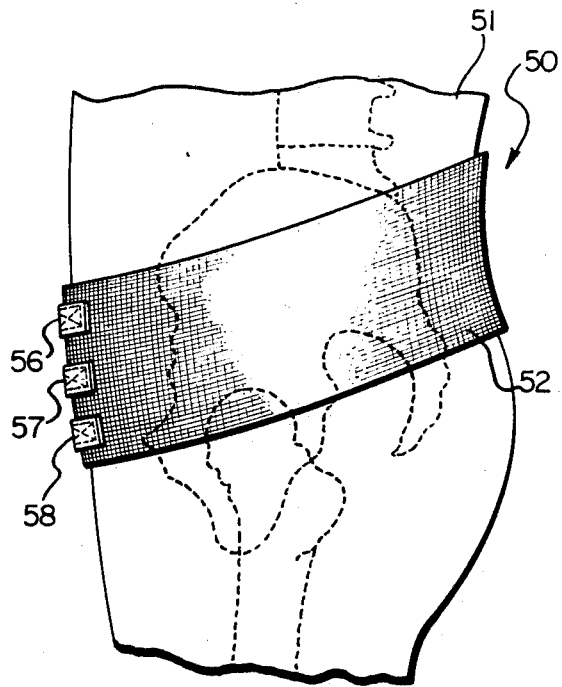
FIG. 4 is a side elevation view of another embodiment of the sacroiliac belt of the present invention, with internal bone structure of the pelvic region shown in phantom.
Figure 5:
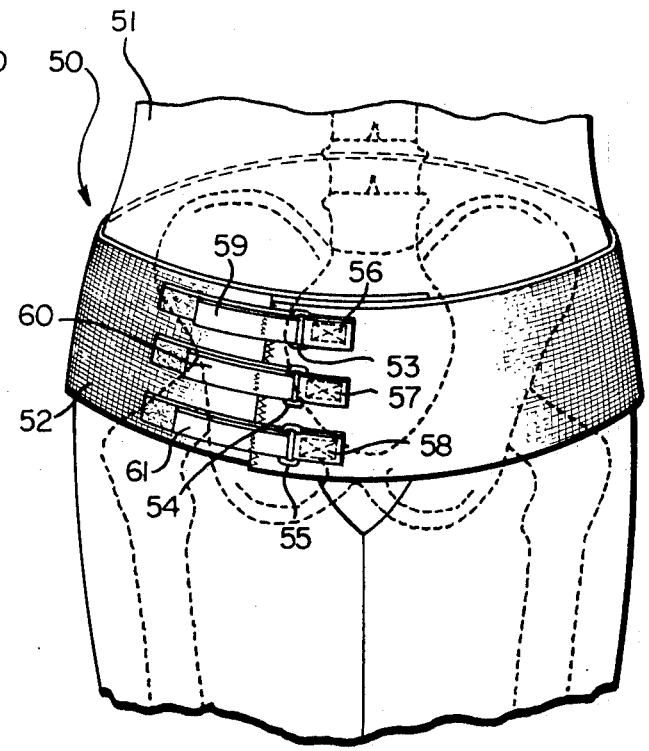
FIG. 5 is a front elevation view similar to FIG. 3, but showing the belt of the embodiment of FIG. 4.

FIGS. 4 and 5 show the present invention embodied in a slightly different belt 50. This belt differs from the belt 10 of FIGS. 1 through 3 in being adapted to a patient 51 having square hips at the level of the sacrum, and in having a band 52 of woven material larger in width. No pads or stays are used. In this embodiment three loops 53, 54 and 55 are held by tabs 56, 57, and 58 substantially aligned with the length of the band 52. Straps 59, 60, and 61 are otherwise identical to the straps 26, 27 of FIGS. 1 through 3. Because the ends of the band 52 meet squarely in the front, no tapering of the ends is necessary.

Other patients will have hip configurations resulting in larger angles 35 than those shown in FIGS. 1 through 3, while others will require angles 35 falling between those of FIGS. 1 through 3 and 4-5. Selection of the length of the belt 10 or 50, of the angle of the tabs 33, 34 or 56-58, and any tapering of the ends to fit individual patients or various ranges of size and shape of patients are easily accomplished, within the scope of the present invention.

The means for fastening the ends of the belts together need not be identical to that shown. Press-holding fabric retainer pads can be applied directly to the ends of the bands. Conventional mechanical belt buckles may be used, either of the pin-in-the-hole type or of the infinitely adjustable toothed clamping type. Ties, snaps, and other devices which protect against loosening of the belt during use may also be employed without departing from the principles of the invention. These and other such minor modifications and variations as are within the ordinary skill of the art and which come within the scope of the following claims are included within the present invention.

We claim as our invention:

1. A belt for easing sacroiliac pain or discomfort in a patient, said belt comprising:

a uniform band of flexible, flat, washable, inelastic, woven fiber webbing material, being generally about 4 to 6 inches in width and having opposite ends spaced apart by a length sufficient to encircle the pelvis of said patient, and wherein the width of said band at each of said ends is tapered at an acute angle to reduce exposure of the free corners at the ends of said band, fastening means comprising at least two hook and loop type pad fasteners, each hook and loop type pad fastener being provided with a strap at one end of the fastener and a buckle at the other end of the fastener whereby each strap is attached to the band parallel to the longitudinal axis of the belt and is inset at a distance from one end of the band sufficient to allow overlapping support in the abdominal region of the user and whereby each buckle is attached substantially at the opposite end of the band at said acute angle to the longitudinal axis of the belt to allow the band to pass horizontally across the patient's pelvis for maintaining compression by the band of the soft tissues of the pelvis firmly against the sacrum, ilium, and coccyx bones of the patient when said straps are passed from one end of said band through the buckle and back upon themselves to be adjustably fastened to themselves with the hook and loop pad fasteners, whereby pain or discomfort in the sacroiliac joint of the human patient may be relieved by a method comprising the steps:

extending the center of said belt horizontally across said patient at the pelvis outwardly of the sacrum, wrapping the ends of said band about the patient at his pelvis, applying sufficient tension to said band at the ends thereof to compress the soft tissue of the pelvis of the patient against the sacrum and ilium to support and substantially immobilize them against relative movement, and joining the ends of the bands together at the front of the patient at an angle to maintain said tension and placement.

* * * * *